(12) United States Patent
Chu et al.

(10) Patent No.: US 7,536,921 B1
(45) Date of Patent: May 26, 2009

(54) TRIAXIAL TESTING APPARATUS HAVING AN IMPROVED BOTTOM SUPPORT OF A SPECIMEN CELL

(76) Inventors: Bin-Lin Chu, No. 250, Guoguang Rd., Taichung City (TW); Lung-Mao Huang, 5F.-5, No. 278, Sec.2, Chongde Rd., Beitun District, Taichung City (TW)

( * ) Notice: Subject to any disclaimer, the term of this patent is extended or adjusted under 35 U.S.C. 154(b) by 0 days.

(21) Appl. No.: 12/030,413

(22) Filed: Feb. 13, 2008

(51) Int. Cl.
*G01N 3/00* (2006.01)

(52) U.S. Cl. .......................................... 73/803; 73/760
(58) Field of Classification Search ................... 73/803, 73/760
See application file for complete search history.

(56) References Cited

U.S. PATENT DOCUMENTS

| | | | | |
|---|---|---|---|---|
| 3,728,895 A | * | 4/1973 | Shaw | 73/819 |
| 4,679,441 A | * | 7/1987 | Johnson et al. | 73/798 |
| 5,226,310 A | * | 7/1993 | Steiger | 73/38 |
| 5,265,461 A | * | 11/1993 | Steiger et al. | 73/38 |
| 6,595,068 B2 | * | 7/2003 | Brovold et al. | 73/803 |
| 7,143,653 B2 | * | 12/2006 | Abdel-Hadi et al. | 73/819 |

* cited by examiner

*Primary Examiner*—Max Noori
(74) *Attorney, Agent, or Firm*—Greenblum & Bernstein, P.L.C.

(57) ABSTRACT

A base beneath a specimen of a specimen cell for triaxial testing includes sealingly interconnected upper and lower covers. The upper cover is perforated, and has a downwardly opening first receiving groove receiving a porous ceramic plate, and a first pressure hole communicated with the first receiving groove. The lower cover has an upwardly opening second receiving groove, and a second pressure hole communicated with the second receiving groove. A non-permeable film is disposed between the upper and lower covers to span the first and second receiving grooves. A guide tube interconnects the first and second pressure holes so that pore air flows to the second receiving groove to provide an upward pressure beneath the film and the ceramic plate. Thus, the pressure difference across the ceramic plate can be reduced to be nearly zero.

13 Claims, 9 Drawing Sheets

TRIAXIAL TESTING APPARATUS HAVING AN IMPROVED BOTTOM SUPPORT OF A SPECIMEN CELL

BACKGROUND OF THE INVENTION

1. Field of the Invention

This invention relates to a triaxial testing apparatus, more particularly to an improved base of a specimen cell of a triaxial testing apparatus.

2. Description of the Related Art

Figure 1:
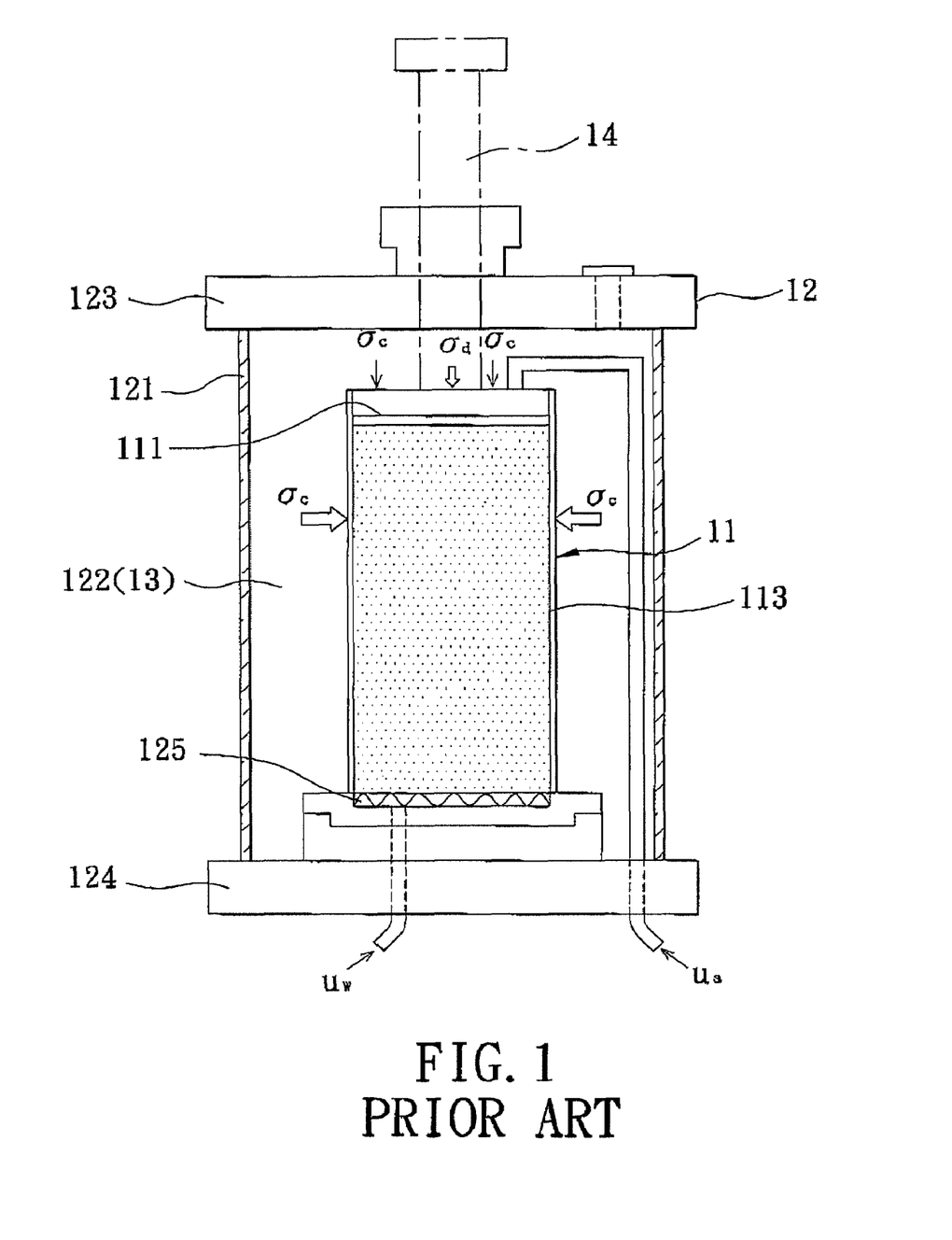
FIG. 1 is a schematic view of a conventional triaxial compression or extension testing apparatus.

FIG. 1 illustrates a conventional triaxial compression or extension testing apparatus for studying the properties of unsaturated soil, gravel and pebble soil, or soft rock. The triaxial compression test is carried out in cooperation with a universal testing machine (not shown), and a triaxial cell 12 which is mounted on the universal testing machine and which accommodates an unsaturated soil specimen that has a size smaller than or equal to 2.5". The triaxial cell 12 has a cylindrical cell body 121 defining a pressure chamber 122, a top seat 123 closing a top end of the pressure chamber 122 and connected to the universal testing machine, and a bottom seat 124 closing a bottom end of the pressure chamber 122. The bottom seat 124 has a porous ceramic plate 125 disposed within the pressure chamber 122. A specimen cell 11 is disposed within the pressure chamber 122, and has a peripheral wall 113 with a bottom end connected to the bottom seat 124, and a top platen 111 disposed on top of the peripheral wall 113. The soil specimen is disposed in the specimen cell 11, and is supported by the porous ceramic plate 125. Pressurized water 13 is disposed within the pressure chamber 122 between the specimen cell 11 and the cell body 121.

The universal testing machine uses a piston 14 to apply an external compression or extension force to the top platen 111 so as to provide a deviator stress $\sigma_d$. The pressurized water 13 provides a confining pressure $\sigma_c$ to the specimen cell 11. During an experiment, a stressor (not shown) provides a pore air pressure $u_a$ through the top platen 111 and a pore water pressure $u_w$ through the porous ceramic plate 125. Since the pore air pressure $u_a$ is greater than the pore water pressure $u_w$, it forces moisture in the soil specimen to flow down to the porous ceramic plate 125.

Although the study of the properties of the unsaturated soil can be achieved using the conventional triaxial compression testing apparatus, the following drawbacks arise:

1. When the diameter of the soil specimen is greater than 2.5" and the compression strength of the soil is high, the deviator stress $\sigma_d$ provided by the universal testing machine is mostly and directly transmitted to the porous ceramic plate 125. Further, when the soil specimen contains granular materials of different mass and size, such as gravel and pebble soil or rock, stress concentration can occur in the porous ceramic plate 125, so that the porous ceramic plate 125 is easily ruptured which leads to test failure.

2. When the pressure difference between the pore air pressure $u_a$ and the pore water pressure $u_w$ is excessively large, the porous ceramic plate 125 is also easily ruptured.

SUMMARY OF THE INVENTION

Therefore, the object of the present invention is to provide a triaxial testing apparatus that has a base capable of protecting a porous ceramic plate of the triaxial testing apparatus from breakage and that is suitable for a triaxial compression or extension test for a soil specimen containing large granular material, such as gravel and pebble soil, or a soft rock specimen.

According to one aspect of this invention, a base of a specimen cell for a triaxial testing apparatus comprises an upper cover, at least one porous ceramic plate, a lower cover, a membrane unit, and a guide tube. The upper cover has a first top face adapted to contact the specimen, a first bottom face recessed to form at least one first receiving groove, at least one group of through holes extending through the first top and bottom faces and connected fluidly to the first receiving groove, and a first pressure hole connected fluidly to the first receiving groove. The porous ceramic plate is disposed in the first receiving groove. The lower cover is disposed below the upper cover, and has a second top face recessed to form a second receiving groove, and a second pressure hole communicating fluidly with the second receiving groove. The membrane unit is disposed between the upper and lower covers, and includes a non-permeable film and a screen stacked on the film. The film and the screen span the first and second receiving grooves. The guide tube fluidly interconnects the first and second pressure holes. The upper and lower covers have outer peripheral ends which are connected sealingly to each other and which extend around the first and second receiving grooves, respectively.

According to another aspect of this invention, a triaxial testing apparatus comprises a specimen cell having a top platen adapted to be disposed on top of a specimen provided within the specimen cell, a base adapted to be disposed beneath the specimen, a pressure tube to apply an air pressure to the specimen cell, and a water tube to introduce a pore water pressure to the specimen cell. The base includes upper and lower covers having outer peripheral ends connected sealingly to each other. The upper cover is perforated, is disposed above the lower cover, and has a first receiving groove that opens downwardly and that connects fluidly to an interior of the specimen cell. The lower cover has a second receiving groove that opens upwardly. The base further includes at least one porous ceramic plate disposed in the first receiving groove, a membrane unit disposed between the upper and lower covers and spanning the first and second receiving grooves to block fluid communication between the first and second receiving grooves, a first pressure hole formed in the upper cover and communicated with the first receiving groove, a second pressure hole formed in the lower cover and communicated with the second receiving groove, a guide tube having two opposite ends connected fluidly and respectively to the first and second pressure holes, and a water inlet hole formed in the upper cover above the membrane unit and connected fluidly to the first receiving groove. The water inlet hole is connected fluidly to the water tube.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Referring to FIGS. 2 to 10, a triaxial testing apparatus according to the preferred embodiment of the present invention is adapted to be applied to a triaxial compression or extension test for the study of soil. The triaxial testing apparatus of the present invention comprises a triaxial cell 24 and a specimen cell 23.

Figure 2:
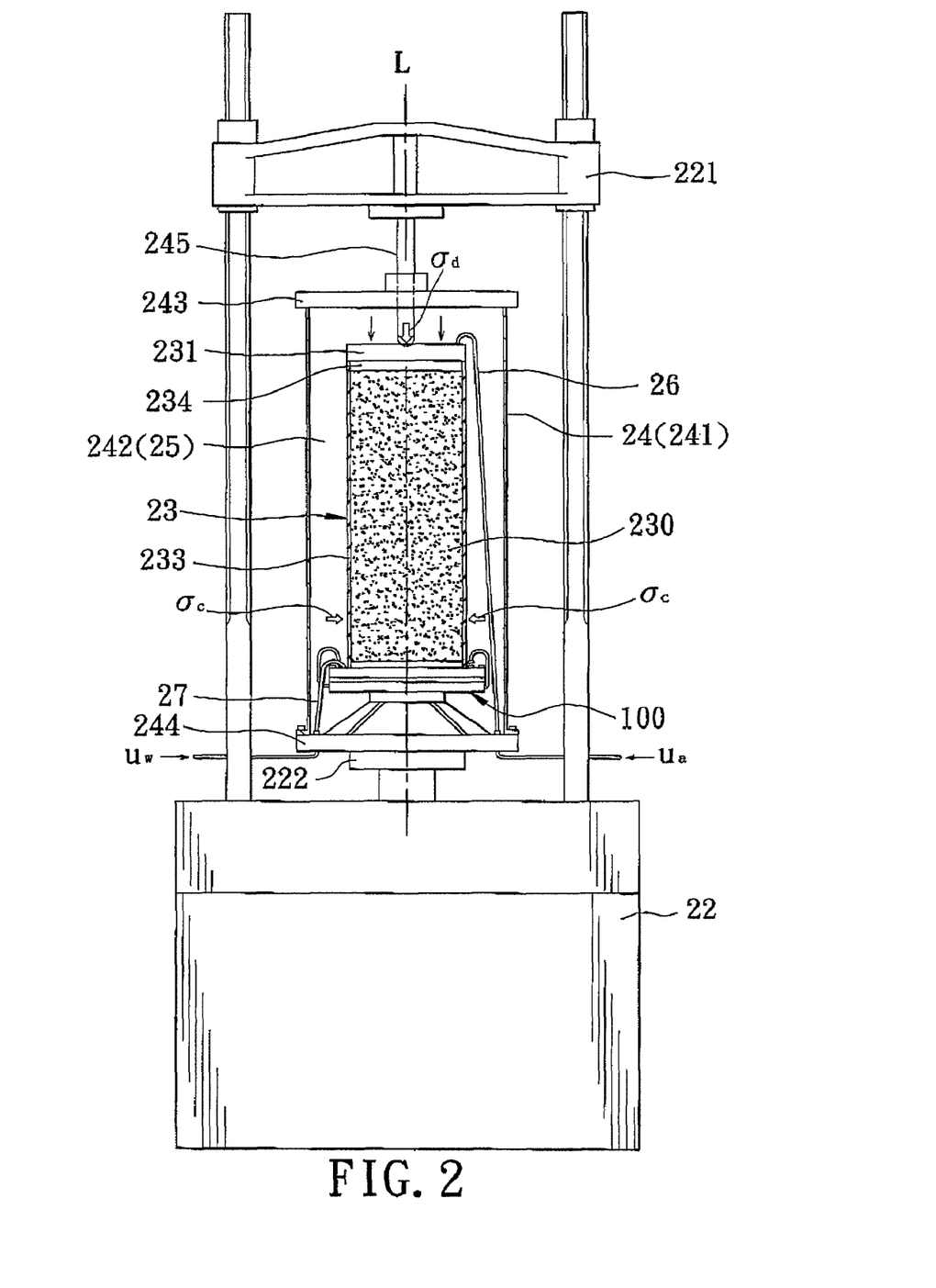
FIG. 2 is a schematic view of a triaxial testing apparatus according to the preferred embodiment of this invention.

The triaxial compression test of the soil is carried out in cooperation with a universal testing machine 22 and a stressor (not shown). The triaxial cell 24 is mounted on the universal testing machine 22, and accommodates a soil specimen 230 that has a diameter larger than 2.5". The stressor provides a pore air pressure $u_a$ and a pore water pressure $u_w$ to the soil specimen 230. The universal testing machine 22 has a fixed end 221 on a top side thereof, and a push end 222 opposite to the fixed end 221. The triaxial cell 24 is disposed between the fixed end 221 and the push end 222, and has a cylindrical cell body 241 defining a pressure chamber 242, a top seat 243 covering a top end of the cell body 241, a push rod 245 connected to the fixed end 221 and extending through the top seat 243, and a bottom seat 244 connected to the push end 222. A bottom end of the cell body 241 is connected to the bottom seat 244.

The specimen cell 23 is disposed within the pressure chamber 242 to receive the soil specimen 230, and has a peripheral wall 233 surrounding the soil specimen 230, a top platen 231 disposed on top of the peripheral wall 233, a permeable stone 234 disposed between the top platen 231 and the soil specimen 230, and a base 100 connected to a bottom opening end of the peripheral wall 233. A bottom end of the push rod 245 abuts against the top platen 231.

When the push end 222 of the universal testing machine 22 is moved upwardly along an axial line (L), it pushes the triaxial cell 24 to move toward the fixed end 221. As the push rod 245 presses the fixed end 221, the fixed end 221 thus applies a deviator stress $\sigma_d$, which is parallel to the axial line (L), against the specimen cell 23. Pressurized water 25 is filled in the pressure chamber 242 between the specimen cell 23 and the cell body 241 to provide the specimen cell 23 with a confining pressure $\sigma_c$.

In this embodiment, the base 100 is connected to the bottom seat 244. Fine sand 21 having a mesh size ranging from 100 mesh to 140 mesh may be used in the base 100 to guide flow of the water content of the soil specimen 230. According to the present invention, the base 100 comprises a perforated upper cover 30, a plurality of porous ceramic plates 40, a lower cover 50, a membrane unit 60, and a pressure regulating device 80.

With reference to FIGS. 3 to 7, the upper cover 30 has a first top face 31, a first bottom face 32 opposite to the first top face 31 and recessed to form a plurality of downwardly opening first receiving grooves 33 (see FIG. 5), an upwardly protruding intermediate portion 311 that extends into the specimen cell 23 through the bottom opening end of the peripheral wall 233 to contact the soil specimen 230, a plurality of groups of through holes 34 extending through the intermediate portion 311 and the first bottom face 32 and communicating fluidly with the respective first receiving grooves 33, a pair of diametrically opposed first pressure holes 35 extending upwardly from two of the first receiving grooves 33 and penetrating the first top face 31 in proximity to an outer peripheral end of the upper cover 30, and a pair of diametrically opposed water inlet holes 36 extending through the first top and bottom faces 31, 32. In this embodiment, the upper cover 30 has seven first receiving grooves 33, and seven groups of the through holes 34. Each group of the through holes 34 communicates fluidly with the respective first receiving grooves 33.

The number of the porous ceramic plates 40 used in this embodiment is seven. Each of the porous ceramic plates 40 is disposed in a respective one of the first receiving grooves 33, and has a bottom face 42 flush with the bottom face 32 of the upper cover 30. The porous ceramic plates 40 are connected fluidly to the through holes 34. In this embodiment, the porous ceramic plates 40 are highly air-permeable and are manufactured by Soilmoisture Equipment Corp.

Figure 3:
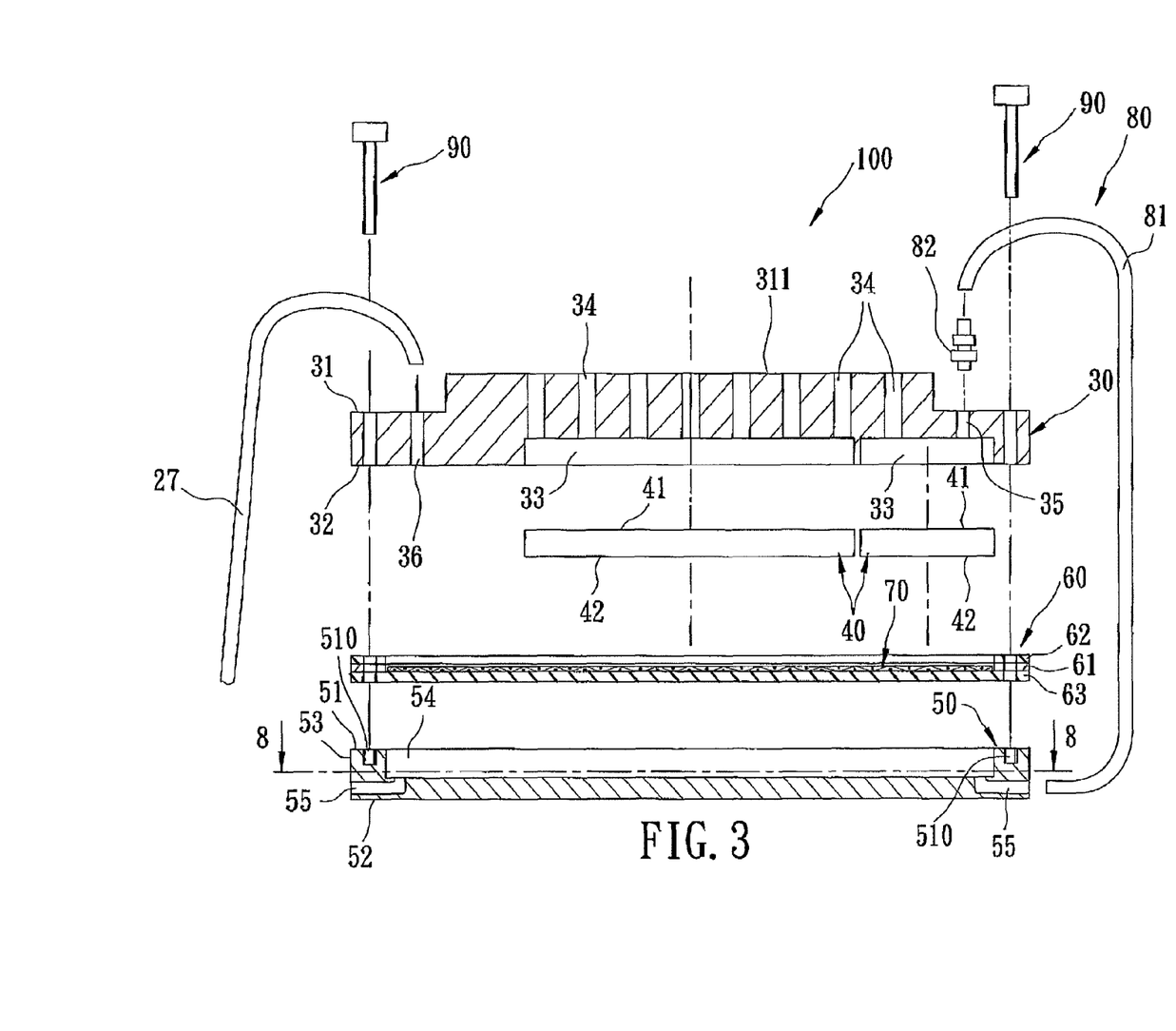
FIG. 3 is an exploded sectional view of a base of the preferred embodiment taken along line 3-3 of FIG. 5.
Figure 4:
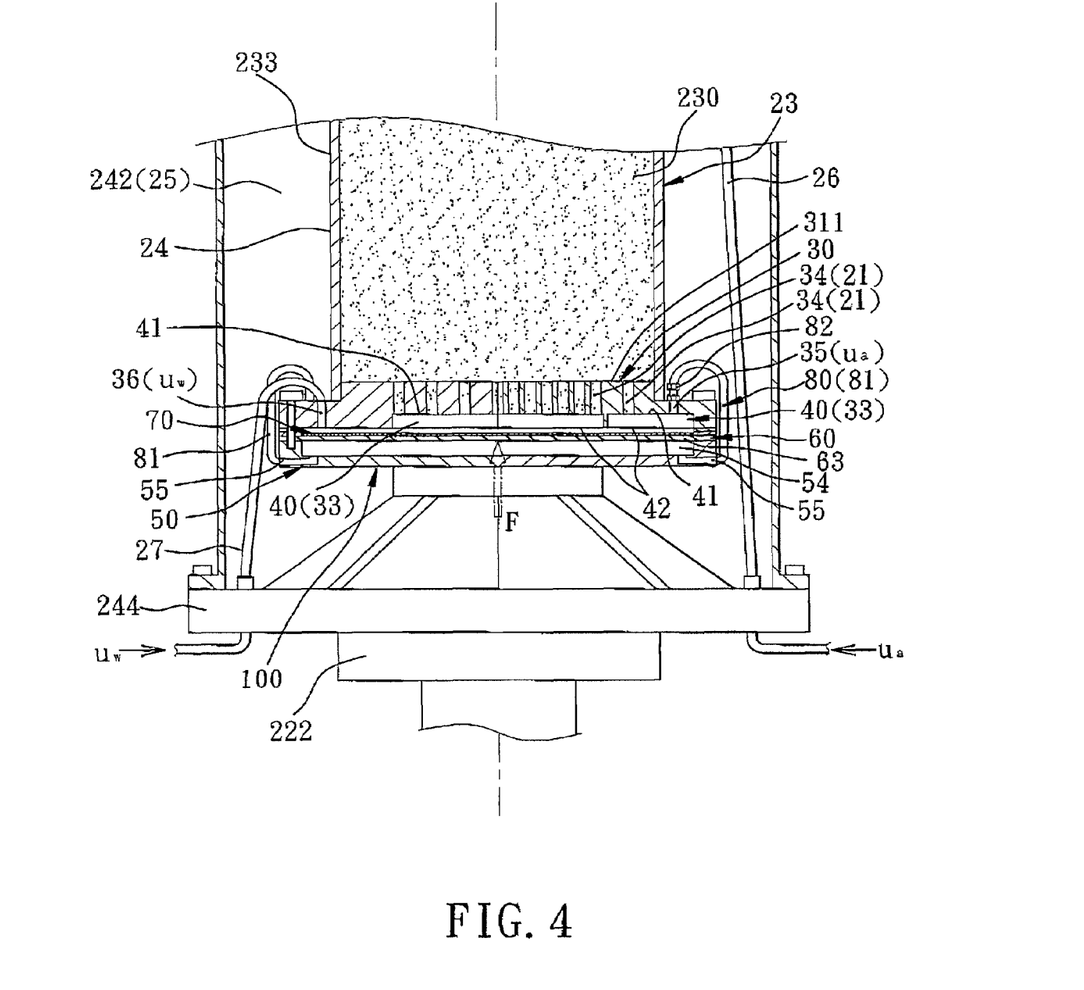
FIG. 4 is a fragmentary sectional view of the preferred embodiment.
Figure 5:
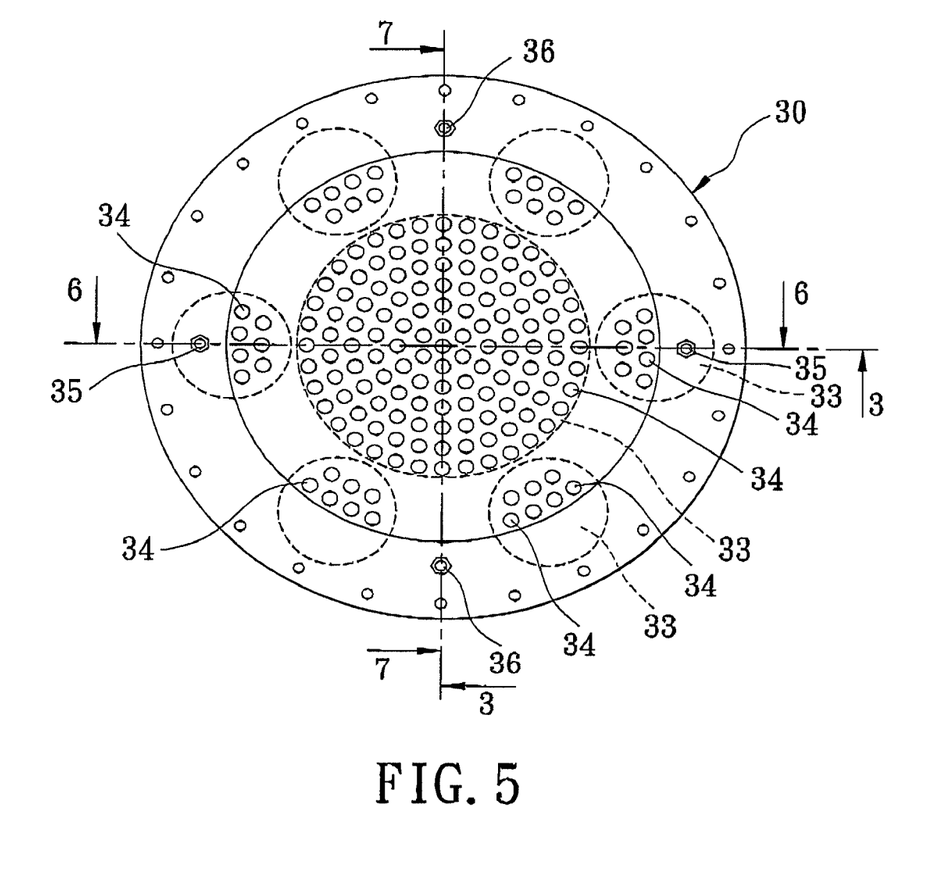
FIG. 5 is a schematic top view of the base of the preferred embodiment.
Figure 6:
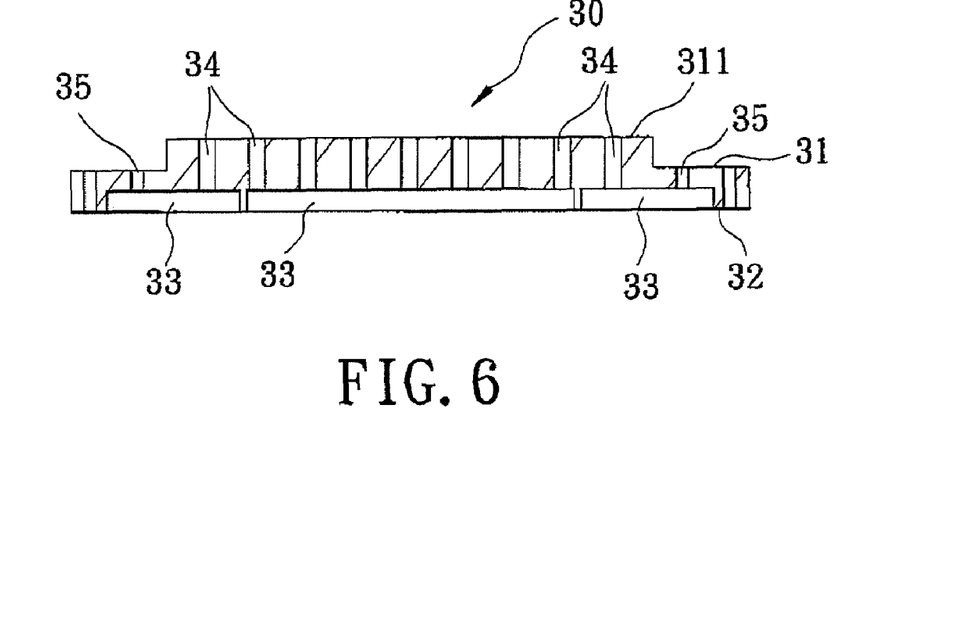
FIG. 6 is a sectional view of the upper cover of the base taken along line 6-6 of FIG. 5.
Figure 7:
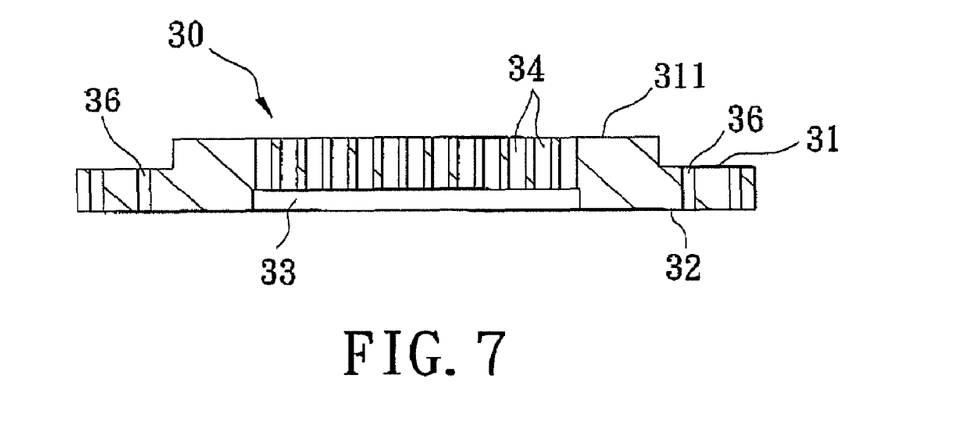
FIG. 7 is a sectional view of the upper cover of the base taken along line 7-7 of FIG. 5.

The fine sand 21 is filled in the through holes 34, and is in contact with the porous ceramic plates 40 and the soil specimen 230. The fine sand 21 can guide the water content of the soil specimen 230 to flow to the top faces 41 of the porous ceramic plates 40. Preferably, if the soil specimen 230 contains a large amount of sand, the fine sand 21 may be of the same kind as that of the soil specimen 230. If the soil specimen 230 is clay which has less sand and if it is difficult to obtain fine sand 21 having a grain size ranging from 100 mesh to 140 mesh, other natural sand may be used.

Figure 8:
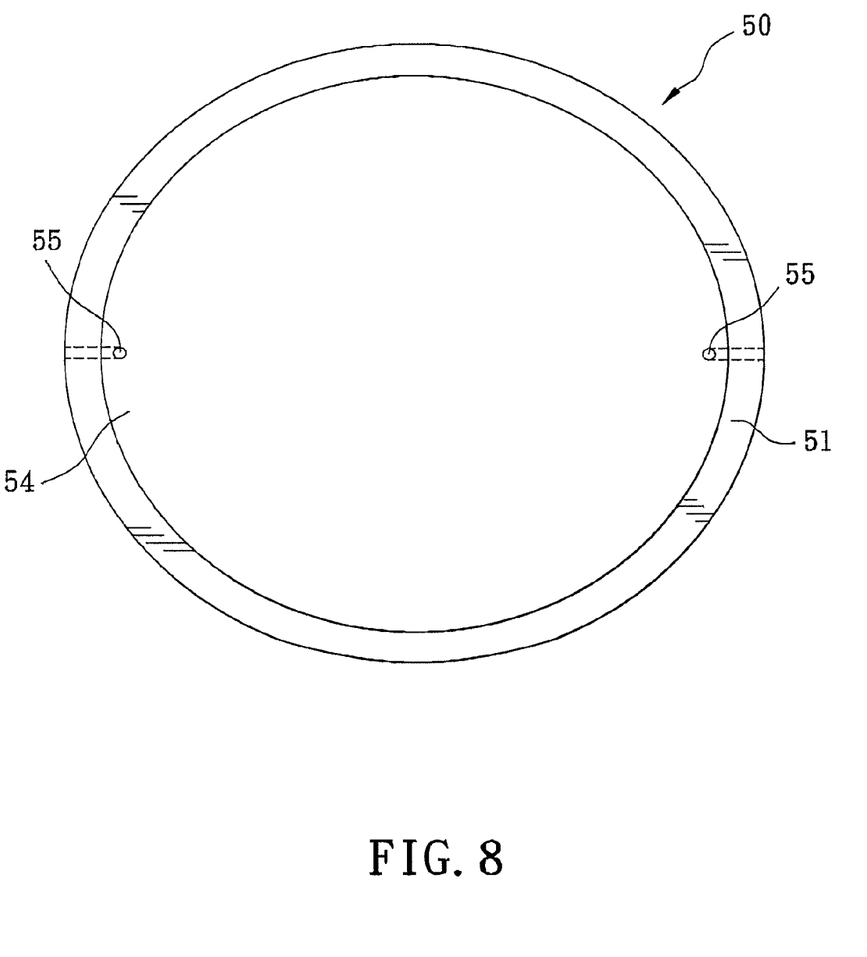
FIG. 8 is a sectional view of a lower cover of the base of the preferred embodiment taken along line 8-8 of FIG. 3.

With reference to FIGS. 3, 4, and 8, the lower cover 50 has a second top face 51 recessed to form an upwardly opening second receiving groove 54, a second bottom face 52 opposite to the second top face 51, an outer peripheral end having a peripheral end face 53 interconnecting the second top and bottom faces 51, 52, and a pair of diametrically opposed second pressure holes 55 extending from a bottom of the second receiving groove 54 to the peripheral end face 53 and communicating fluidly with the second receiving groove 54. The outer peripheral ends of the upper and lower covers 30, 50 extend around the first and second receiving grooves 33, 54, respectively. Each of the upper and lower covers 30, 50 may be made of a metallic material selected from the group consisting of copper, stainless steel, a corrosion-resistant alloy, and a plated metal.

Figure 9:
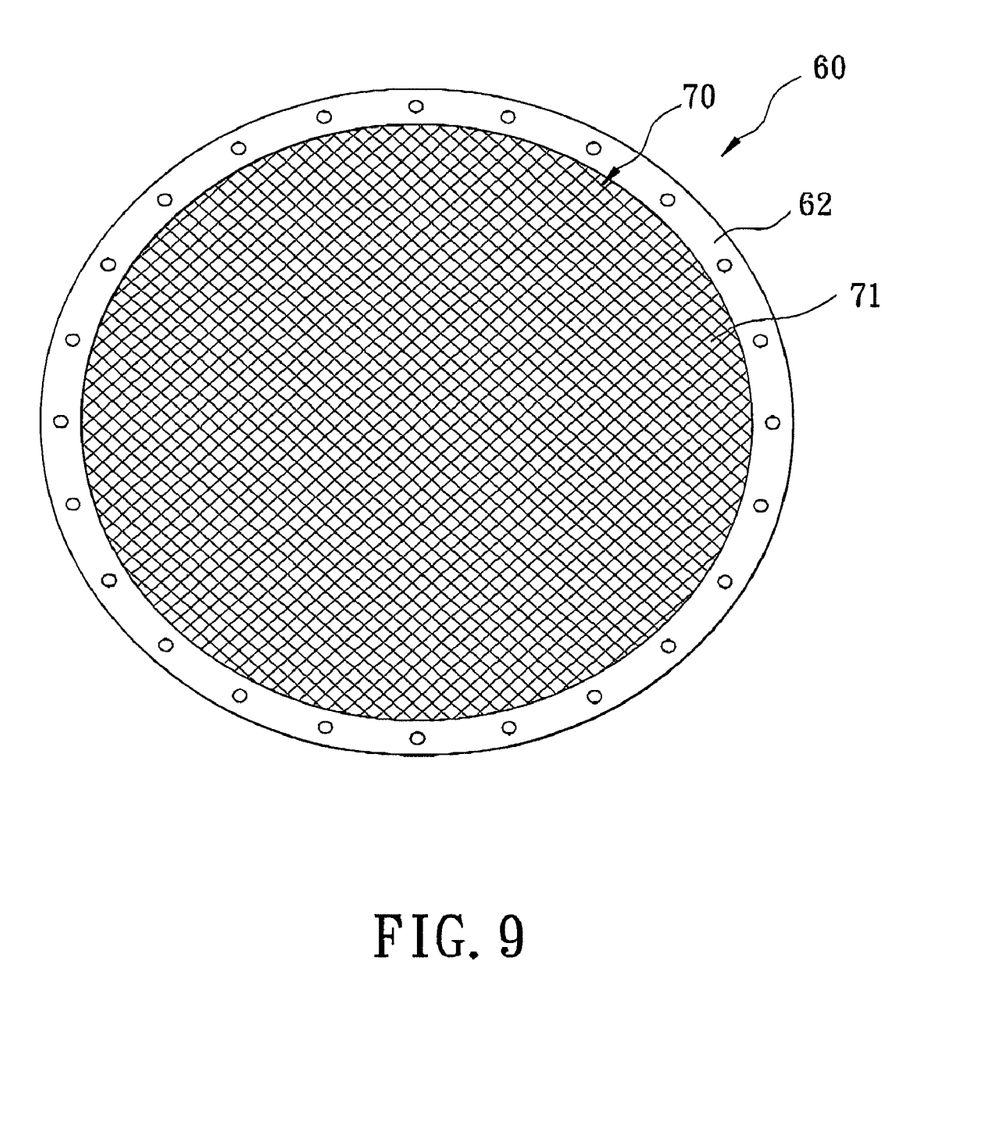
FIG. 9 is a schematic top view of a membrane unit of the base of the preferred embodiment.
Figure 10:
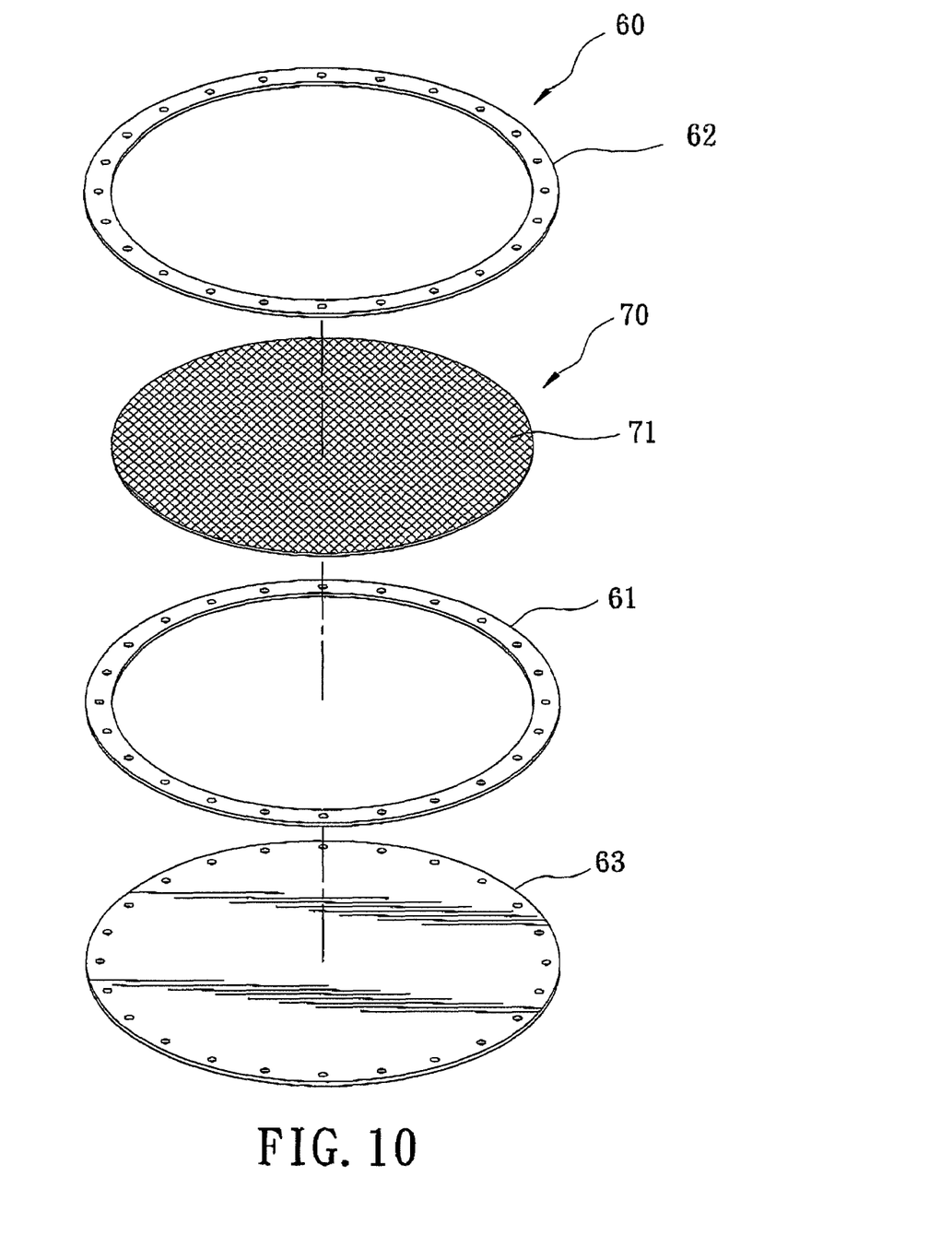
FIG. 10 is an exploded perspective view of the membrane unit of the base of the preferred embodiment.

With reference to FIGS. 9 and 10, in combination with FIG. 3, the membrane unit 60 is disposed between the upper and lower covers 30, 50, and includes a metallic sealing ring 61, a rubber sealing ring 62 superimposed on the metallic sealing ring 61, a non-permeable film 63 having an outer peripheral end extending between the outer peripheral ends of the upper and lower covers 30, 50, and a screen 70 stacked on the film 63. The metallic and rubber sealing rings 61, 62 are disposed between the outer peripheral ends of the upper cover 30 and the film 63. The screen 70 is disposed within the metallic and rubber sealing rings 61, 62, and has a plurality of perforations 71 to permit horizontal and vertical flowing of the soil water content. The film 63 and the screen 70 span the first and second receiving grooves 33, 54 so as to block fluid communication from the first receiving grooves 33 to the second receiving groove 54 and vice versa. Each of the film 63 and the screen 70 may be made of a material selected from the group consisting of plastic and rubber.

The water inlet holes 36 are disposed above the membrane unit 60, and communicate fluidly with the first receiving grooves 33 through the metallic and rubber sealing rings 61, 62. The outer peripheral ends of the upper and lower covers 30, 50 are connected sealingly to each other through use of a plurality of screws 90 that pass through the first top and bottom faces 31, 32, the metallic and rubber sealing rings 61, 62, and the film 63, and engage threadedly screw holes 510 formed in the second top face 51.

With reference to FIGS. 2, 3, and 4, the pressure regulating device 80 includes a pair of guide tubes 81 and a plurality of connectors 82. Each of the guide tubes 81 has one end connected fluidly to the first pressure holes 35 through the corresponding connector 82, and the other end connected fluidly to one of the second pressure holes 55. Each guide tube 81 thus extends to the peripheral end face of the lower cover 50 for connection with the respective second pressure hole 55, and also extends to the first top face 31 for connection with the respective first pressure hole 35.

The stressor (not shown) provides a pore air pressure $u_a$ by means of a pressure tube 26 that extends through the top platen 231 of the specimen cell 23, and provides a pore water pressure $u_w$ through a water tube 27 that is connected to the two water inlet holes 36. The pore air pressure $u_a$ is gradually spread from the top platen 231 of the specimen cell 23 to the soil specimen 230, the fine sand 21, and the porous ceramic plates 40. Since the pore air pressure $u_a$ is greater than the pore water pressure $u_w$, there is a difference between the pressure on the top and bottom faces 41, 42 of the porous ceramic plates 40, and the water content in the soil specimen 230 thus flows gradually to the top faces 41 of the porous ceramic plates 40 through the fine sand 21. Further, from the top faces 41 of the porous ceramic plates 40, the water content of the soil specimen 230 flows between the bottom faces 42 of the porous ceramic plates 42 and the film 63 and between the perforations 71 of the screen 70.

On the other hand, because the guide tubes 81 establish a fluid communication between the first and second receiving grooves 33, 54, the pore air pressure $u_a$ above the top faces 41 of the porous ceramic plates 40 is guided to the second receiving groove 54 through the guide tubes 81. Therefore, the first and second receiving grooves 33, 54 have substantially the same pressure. In other words, an upward pressure (F) generated in the second receiving groove 54 below the film 63 is substantially equal to the pore air pressure $u_a$ existing above the porous ceramic plates 40, and the pressure difference across the porous ceramic plates 40 is nearly zero. Since the film 63 is non-permeable, and since no air exists between the film 63 and the porous ceramic plates 40, the film 63 is substantially adhered to the bottom faces 42 of the porous ceramic plates 40.

It is worth mentioning that the seven porous ceramic plates 40 may be replaced by a single large porous ceramic plate (not shown) that may cooperate with a single first receiving groove and a single group of through holes. A similar effect to that described above may be obtained through such a configuration. However, when a plurality of the separate porous ceramic plates 40 each having a small area are used, breakage of the porous ceramic plates 40 may be minimized even when the upper cover 30 deforms due to a large deviator stress.

By using the upper and lower covers 30, 50 to cover the porous ceramic plates 40, and by using the pressure regulating device 80 to minimize a pressure difference across the porous ceramic plates 40, during the triaxial compression test of the soil, even if the diameter of the soil specimen 230 is above 9", the porous ceramic plates 40 maintain their integrity and do not come close to being ruptured.

From the aforementioned description, the advantages of the present invention may be summarized as follows:

1. Since the porous ceramic plates 40 are disposed between the upper and lower covers 30, 50 which are made of metal, and since the upper and lower covers 30, 50 can assist in supporting the soil specimen 230, even if the compression strength of the soil specimen 230 is high, or even if the granular size of the soil specimen 230 is not uniform due to the presence of gravel and pebble soil or soft rock, rupturing of the porous ceramic plates 40 due to a stress concentration can be minimized.

2. Since the pressure difference across the porous ceramic plates 40 is nearly zero, the porous ceramic plates 40 can be prevented from being ruptured.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

We claim:

1. A base of a specimen cell for a triaxial testing apparatus, comprising;
    an upper cover having a first top face adapted to contact the specimen, a first bottom face recessed to form at least one first receiving groove, at least one group of through holes extending through said first top and bottom faces and connected fluidly to said first receiving groove, and a first pressure hole connected fluidly to said first receiving groove;
    at least one porous ceramic plate disposed in said first receiving groove;
    a lower cover disposed below said upper cover and having a second top face recessed to form a second receiving groove, and a second pressure hole communicating fluidly with said second receiving groove;
    a membrane unit disposed between said upper and lower covers, and including a non-permeable film and a screen stacked on said film, said film and said screen spanning said first and second receiving grooves; and
    a guide tube fluidly interconnecting said first and second pressure holes;
    wherein said upper and lower covers have outer peripheral ends which are connected sealingly to each other and which extend around said first and second receiving grooves, respectively.

2. The base of claim 1, wherein said non-permeable film has an outer peripheral end extending between said outer peripheral ends of said upper and lower covers.

3. The base of claim 2, wherein said membrane unit further includes at least one sealing ring disposed between said outer peripheral ends of said upper cover and said film, said screen being disposed within said sealing ring.

4. The base of claim 2, wherein said membrane unit further includes a metallic sealing ring, and a rubber sealing ring superimposed on said metallic sealing ring, said rubber and metallic sealing rings being disposed between said outer peripheral ends of said upper cover and said film, said screen being disposed within said rubber and metallic sealing rings.

5. The base of claim 1, wherein said upper cover has a plurality of said first receiving grooves, a plurality of groups of said through holes, and a plurality of said porous ceramic plates, each of said groups of said through holes being connected fluidly to a corresponding one of said first receiving grooves, each of said first receiving grooves receiving one of said porous ceramic plates.

6. The base of claim 5, wherein a pair of said guide tubes are provided, said upper cover having a pair of said first pressure holes, said lower cover having a pair of said second pressure holes, each of said guide tubes connecting one of said first pressure holes to one of said second pressure holes.

7. The base of claim 1, wherein said first top face of said upper cover has an upwardly extending intermediate portion that is adapted to contact the specimen.

8. The base of claim 1, wherein said first pressure hole extends upwardly from said first receiving groove and penetrates said first top face in proximity to said outer peripheral end of said upper cover.

9. The base of claim 8, wherein said lower cover further has a second bottom face opposite to said second top face, said outer peripheral end of said lower cover has a peripheral end face that interconnects said second top and bottom faces, said second pressure hole extending from a bottom of said second receiving groove to said peripheral end face, said guide tube having one end extending to said peripheral end face of said lower cover for connection with said second pressure hole, and the other end extending to said first top face for connection with said first pressure hole.

10. The base of claim 1, wherein each of said upper and lower covers is made of a metallic material selected from the group consisting of copper, stainless steel, a corrosion-resistant alloy, and a plated metal.

11. The base of claim 1, wherein said film is made of a material selected from the group consisting of plastic and rubber.

12. The base of claim 1, wherein said screen is made of a material selected from the group consisting of plastic and rubber.

13. A triaxial testing apparatus, comprising;
a specimen cell having a top platen adapted to be disposed on top of a specimen provided within said specimen cell, a base adapted to be disposed beneath the specimen, a pressure tube to apply an air pressure to said specimen cell, and a water tube to introduce a pore water pressure to said specimen cell;
said base including upper and lower covers having outer peripheral ends connected sealingly to each other, said upper cover being perforated, being disposed above said lower cover, and having a first receiving groove that opens downwardly and that connects fluidly to an interior of said specimen cell, said lower cover having a second receiving groove that opens upwardly;
said base further including at least one porous ceramic plate disposed in said first receiving groove, a membrane unit disposed between said upper and lower covers and spanning said first and second receiving grooves to block fluid communication between said first and second receiving grooves, a first pressure hole formed in said upper cover and communicated with said first receiving groove, a second pressure hole formed in said lower cover and communicated with said second receiving groove, a guide tube having two opposite ends connected fluidly and respectively to said first and second pressure holes, and a water inlet hole formed in said upper cover above said membrane unit and connected fluidly to said first receiving groove, said water inlet hole being connected fluidly to said water tube.

* * * * *